(12) United States Patent
Yoshimoto et al.

(10) Patent No.: US 7,550,649 B2
(45) Date of Patent: Jun. 23, 2009

(54) TRANSGENIC NON-HUMAN MAMMAL

(75) Inventors: Makoto Yoshimoto, Tokyo (JP); Masaki Wakamatsu, Saitama (JP); Aiko Ishii, Saitama (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 23 days.

(21) Appl. No.: 10/577,302

(22) PCT Filed: Oct. 28, 2004

(86) PCT No.: PCT/JP2004/016373

§ 371 (c)(1),
(2), (4) Date: Jan. 3, 2007

(87) PCT Pub. No.: WO2005/041649

PCT Pub. Date: May 12, 2005

(65) Prior Publication Data

US 2007/0192879 A1    Aug. 16, 2007

(30) Foreign Application Priority Data

Oct. 30, 2003  (JP)  ............................. 2003-370507
Mar. 22, 2004  (JP)  ............................. 2004-082637

(51) Int. Cl.
*A01K 67/027*  (2006.01)
*A01K 67/00*  (2006.01)

(52) U.S. Cl. ............................. 800/18; 800/8

(58) Field of Classification Search .................. 800/8, 800/18, 3
See application file for complete search history.

(56) References Cited

U.S. PATENT DOCUMENTS

| | | |
|---|---|---|
| 6,504,080 B1 | 1/2003 | Van der Putten |
| 2002/0111321 A1 | 8/2002 | Klein et al. |
| 2003/0056231 A1 | 3/2003 | Masliah et al. |
| 2003/0217370 A1 | 11/2003 | Giasson et al. |
| 2004/0128706 A1 | 7/2004 | Maslian et al. |
| 2004/0205833 A1 | 10/2004 | Klein et al. |
| 2005/0086711 A1 | 4/2005 | Masliah et al. |
| 2005/0198694 A1 | 9/2005 | Chilcote et al. |
| 2006/0259986 A1 | 11/2006 | Chilcote et al. |
| 2007/0157324 A1 | 7/2007 | Klein et al. |

FOREIGN PATENT DOCUMENTS

| | | |
|---|---|---|
| JP | 2003-199460 | 7/2003 |
| WO | 98/59050 | 12/1998 |
| WO | 00/20020 | 4/2000 |
| WO | 02/49422 | 6/2002 |
| WO | 01/60794 | 8/2002 |
| WO | 02/063951 | 8/2002 |
| WO | 03/015507 | 2/2003 |
| WO | 2005/013889 | 2/2005 |

OTHER PUBLICATIONS

Matsuoka (Neurobiology of Disease, Jun. 2001, vol. 8, p. 535-539.*
Rathke-Hartlieb (J. Neurochem., 2001, vol. 77, p. 1181-1184).*
Masliah (Science, Feb. 2000, vol. 287, p. 1265-1268).*
Wall (1996, Theriogenology, vol. 45, p. 57-68).*
Ebert (1988, Mol. Endocrinology, vol. 2, pp. 277-283).*
Mullins (1990, Nature, vol. 344, p. 541-544).*
Hammer (1990, Cell, vol. 63, p. 1099-1112).*
Mullins, 1989, EMBO, vol. 8, p. 4065-4072.*
Taurog, 1988, J. Immunol., vol. 141, p. 4020-4023.*
K. Kobayashi et al., Proceedings of the National Academy of Sciences USA, vol. 89, pp. 1631-1635.
B.I. Giasson et al., Neuron, 2002, vol. 34, pp. 521-533.
P.J. Kahle et al., The Journal of Neuroscience, 2000, vol. 20, No. 17, pp. 6365-6373.
M.K. Lee et al., Proc. Natl. Acad. Sci USA, 2002, vol. 99, No. 13, pp. 8968-8973.
M. Neumann et al., J Clin Invest, 2002, vol. 110, No. 10, pp. 1429-1439; M.H. Polymeropoulos, Science, 1997, vol. 276, pp. 2045-2047.
R. Krueger et al., Nature Genetics, 1998, vol. 18, No. 2, pp. 106-108.
T. Iwawaki et al., Biochem Biophys Res Commun, 2000, vol. 274, pp. 590-595.
K. Wakabayashi et al., Acta Neuropathol, 2000, vol. 99, pp. 14-20.
E. Masliah, Science, 2000, vol. 287, pp. 1265-1269.
Y. Matsuoka, Neurobiology of Disease, 2001, vol. 8, pp. 535-539.
E.K. Richfield, Experimental Neurology, 2002, vol. 175, pp. 35-48.
H. van der Putten, The Journal of Neuroscience, 2000, vol. 20, No. 16, pp. 6021-6029.
W. Zhou et al., Brain Research, 2002, vol. 926, pp. 42-50.
S. Kanda et al., Neuroscience, 2000, vol. 97, No. 2, pp. 279-284.
S.M. Park et al., The Journal of Biological Chemistry, 2002, vol. 277, No. 32, pp. 28512-28520.
P.-O. Fernagut et al., Neurobiology of Disease, 2004, vol. 17, pp. 123-130.
Ishi, et al., Bulletin of the Japanese Society for Neuroscience, Aug. 10, 2004, 43(2,3), p. 369, OGI-08.
D. Kirik et al, Proc. Natl. Acad. Sci. USA, 2003, 100(5), pp. 2884-2889.
C.L. Bianco et al., Proc. Natl. Acad. Sci. USA, 2002, 99(16), pp. 10813-10818.
T.D. Kim et al., Biochemistry, 2002, 41(46), pp. 13782-13790.

\* cited by examiner

*Primary Examiner*—Michael C. Wilson
(74) *Attorney, Agent, or Firm*—Greenblum & Bernstein, P.L.C.

(57) ABSTRACT

An object of the present invention is to provide a model animal of Parkinson's disease comprising an α-synuclein gene introduced therein. The present invention provides a transgenic non-human mammal or a portion thereof, wherein an α-synuclein gene is introduced and the gene is expressed in neurons, and the number of dopamine-producing neurons in the substantial nigra is significantly decreased as compared with that of a wild-type animal.

2 Claims, 8 Drawing Sheets

A

B

TRANSGENIC NON-HUMAN MAMMAL

TECHNICAL FIELD

The present invention relates to a transgenic non-human mammal comprising an α-synuclein gene introduced therein. More specifically, the present invention relates to a transgenic non-human mammal characterized in that the α-synuclein gene is expressed in the brain, and the number of dopamine neurons in the substantial nigra is significantly decreased as compared with that of a wild-type animal, and to use thereof.

BACKGROUND ART

Parkinson's disease is one of neurodegenerative disorders found in adults and elderly people. Parkinson's disease generally displays impaired motor functions, and one of the pathologic changes observed in Parkinson's disease is the degeneration or disappearance of dopamine neurons in the substantial nigra. Selective reduction in the dopamine level of a midbrain-basal ganglion system caused by this pathologic change can be suppressed by orally administered L-dopa, a dopamine precursor. Improvement in the symptoms is seen by this administration. Thus, L-dopa and dopamine receptor agonists are used as therapeutic drugs for Parkinson's disease. However, the administration of the dopamine precursor serves as merely a symptomatic therapy. The symptoms gradually progress, and the efficacy of these drugs declines. Therefore, in the end, patients with Parkinson's disease die in many cases.

Moreover, one of the pathological characteristics of Parkinson's disease is the appearance of Lewy bodies. Lewy body is a specific inclusion body that intracellularly appears in remaining neurons in the substantial nigra, locus coeruleus nucleus, vagus nerve nucleus, and so on. Furthermore, dementia with Lewy bodies (DLB) is also known as a disease in which Lewy bodies appear in the cerebral cortex, in addition to in the affected part of the brain stem.

While most cases of Parkinson's disease are sporadic, there exists a family line with autosomal dominant inheritance on rare occasions. From linkage analysis on family lines with familial Parkinson's disease, an α-synuclein gene located on the long arm of chromosome 4 was identified as a causative gene of Parkinson's disease, and missense mutations (A53T and A30P) in the gene were also confirmed (Polymeropoulos MH, et al., Science 1997 Jun. 27; 276 (5321): 2045-7; and Kruger R, et al., Ala30Pro mutation in the gene encoding alpha-synuclein in Parkinson's disease. Nat Genet. 1998 Feb; 18 (2): 106-8). Subsequent biochemical studies and immunohistological studies using anti-α-synuclein antibodies have revealed that Lewy bodies in sporadic Parkinson's disease and DLB are the result of accumulation of α-synuclein, and have shown the importance of accumulation of α-synuclein as a cause of Parkinson's disease.

Although transgenic animals that overexpress wild-type or variant α-synuclein have previously been reported as model mice of Parkinson's disease (International Publications WO 01/60794 and WO 98/59050, etc.), no previous report has described a transgenic animal whose intracerebral dopamine level is significantly decreased immediately after birth. Moreover, there has been no report about a transgenic animal in which the degeneration or disappearance of dopamine neurons in the substantial nigra, particularly the pathological feature of Parkinson's disease, that is, the degeneration or disappearance of dopamine neurons in the substantial nigra pars compacta is observed, while no change in the ventral tegmental area is observed.

DISCLOSURE OF THE INVENTION

A problem to be solved by the present invention is to provide a model animal of Parkinson's disease comprising an α-synuclein gene introduced therein. A further problem to be solved by the present invention is to provide a method of screening a substance having dopamine-like action by using the model animal.

The present inventors have conducted diligent studies for solving the aforementioned problems and have generated a transgenic mouse by utilizing, as a transgene, a variant gene that is varied from a wild-type human α-synuclein gene in a manner that substitutes a Thr residue for an Ala residue at amino acid residue 53 in an amino acid sequence encoded by the wild-type human α-synuclein gene and in a manner that deletes C terminal amino acid residues. Furthermore, the present inventors have analyzed the generated transgenic mouse for its intracerebral dopamine level, tyrosine hydroxylase expression level, and spontaneous locomotor activity, and so on, and have consequently confirmed that the transgenic mouse is a mouse with high usefulness as a model animal of Parkinson's disease. The present invention has been completed based on these findings.

Namely, the Present Invention Provides the Following Inventions:

(1) A transgenic non-human mammal or a portion thereof, wherein an α-synuclein gene is introduced and the gene is expressed in the neurons, and the number of dopamine neurons in the substantial nigra is significantly decreased as compared with that of a wild-type animal.

(2) The transgenic non-human mammal or a portion thereof according to (1), wherein the α-synuclein gene is a human α-synuclein gene or a variant thereof.

(3) The transgenic non-human mammal or a portion thereof according to (1) or (2), wherein the α-synuclein gene is a variant of a wild-type human α-synuclein gene in a manner that substitutes a Thr residue for an Ala residue at amino acid residue 53 in an amino acid sequence encoded by the wild-type human α-synuclein gene.

(4) The transgenic non-human mammal or a portion thereof according to any of (1) to (3), wherein the α-synuclein gene is a gene that is varied from a wild-type α-synuclein gene in a manner that deletes C terminal amino acid residues encoded by the wild-type α-synuclein gene.

(5) The transgenic non-human mammal or a portion thereof according to any of (1) to (4), wherein a recombinant DNA incorporating the α-synuclein gene therein under the control of a promoter capable of expressing the α-synuclein gene in the dopamine neurons is introduced.

(6) The transgenic non-human mammal or a portion thereof according to any of (1) to (5), wherein the promoter capable of expressing the α-synuclein gene in the dopamine neurons is a tyrosine hydroxylase promoter.

(7) The transgenic non-human mammal or a portion thereof according to any of (1) to (6), wherein an intracerebral dopamine level at an early age is significantly decreased as compared with that of a wild-type animal.

(8) The transgenic non-human mammal or a portion thereof according to any of (1) to (7), wherein an intracerebral dopamine level at an early age is decreased to 85% or less as compared with that of a wild-type animal.

(9) The transgenic non-human mammal or a portion thereof according to any of (1) to (8), wherein a tyrosine hydroxylase expression level is decreased to 80% or less as compared with that of a wild-type animal.

(10) The transgenic non-human mammal or a portion thereof according to any of (1) to (9), wherein a spontaneous locomotor activity is decreased to 60% or less as compared with that of a wild-type animal.

(11) The transgenic non-human mammal or a portion thereof according to any of (1) to (10), wherein the non-human mammal is a mouse.

(12) A method for screening a substance having dopamine-like action wherein the non-human mammal or a portion thereof according to any of (1) to (11) is used.

(13) The screening method according to (12), wherein the substance having dopamine-like action is a therapeutic agent or preventive agent for Parkinson's disease.

(14) A substance obtained by the screening method according to (12) or (13).

(15) A therapeutic agent or preventive agent for Parkinson's disease which comprises a substance obtained by the screening method according to (12) or (13), as an active ingredient.

BRIEF DESCRIPTION OF THE DRAWINGS

FIG. 2A: the analysis of a copy number of the gene incorporated in the chromosome by Southern hybridization. FIG. 2B: the analysis of gene expression in the brain by Northern hybridization. FIG. 2C: the analysis of variant human α-synuclein by Western blotting;

FIG. 11A: an actual measurement value of the number of cells. FIG. 11B: the quantification of tyrosine hydroxylase-positive regions by image analysis (light area: the substantial nigra pars compacta, dark area: the ventral tegmental area).

BEST MODE FOR CARRYING OUT THE INVENTION

Figure 1:
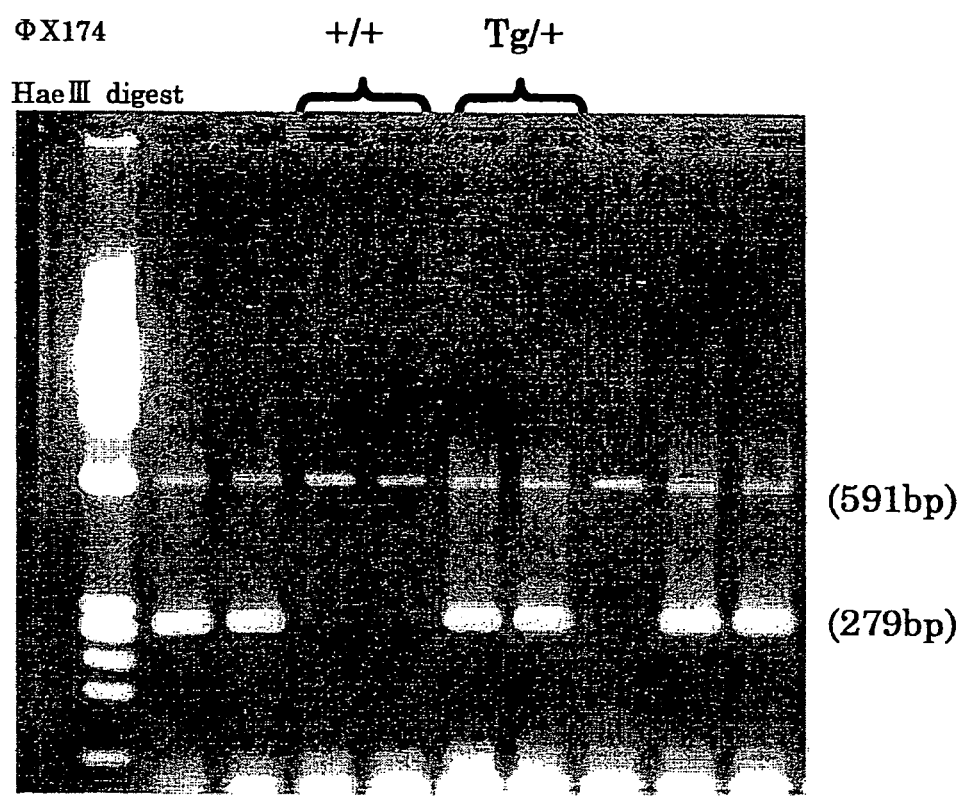
FIG. 1 shows the selection of a transgenic mouse that expresses variant human α-synuclein by PCR. An individual for which both of a 279-bp band and a 519-bp band can be detected is the desired transgenic mouse.

Hereinafter, the embodiments of the present invention will be described in detail.

(1) Characteristics of Transgenic Non-Human Mammal of the Present Invention

The transgenic non-human mammal of the present invention is characterized in that an α-synuclein gene is introduced and the gene is expressed in the neurons, and the number of dopamine neurons in the substantial nigra is significantly decreased as compared with that of a wild-type animal. According to a particularly preferred aspect, the transgenic non-human mammal of the present invention has any one or more of the following characteristics:

(1) The intracerebral dopamine level at an early age is significantly decreased as compared with that of a wild-type animal. Preferably, the intracerebral dopamine level at 8 weeks of age is decreased to 85% or less, more preferably 70% or less, even more preferably 60% or less, as compared with that of a wild-type animal.

(2) The number of dopamine neurons in the substantial nigra pars compacta is decreased as compared with that of a wild-type animal, whereas the number of dopamine neurons in the ventral tegmental area is not changed.

(3) The tyrosine hydroxylase expression level is decreased to 80% or less, preferably 70% or less, more preferably 60% or less, as compared with that of a wild-type animal.

(4) The spontaneous locomotor activity is decreased to 60% or less, preferably 50% or less, as compared with that of a wild-type animal.

In the present specification, the "early age" means an age on the order of 5 days to 1 year of age after birth.

For the transgenic non-human mammal of the present invention, the intracerebral dopamine level can be determined, for example, by preparing a dopamine-containing sample from the brain tissue and analyzing the sample by HPLC or the like. Moreover, the number of dopamine neurons in the substantial nigra can be determined by measuring the number of tyrosine hydroxylase-positive cells. Furthermore, the tyrosine hydroxylase expression level can be determined by Northern blotting, RT-PCR, or immunohistological staining, or the like. Besides, the motor function and spontaneous locomotor activity can be determined by a method described herein in Examples 10 and 11 or an equivalent method thereof.

The "α-synuclein gene" described herein is a gene known in the art. Any of α-synuclein genes from mammals such as humans and variant genes having the same function as with these genes can be employed as the α-synuclein gene used in the present invention. The amino acid sequence encoded by the human α-synuclein gene is described in SEQ ID NO: 16 of the sequence listing.

In the present invention, a variant gene of the α-synuclein gene can also be employed. The variant gene means any of those derived from the α-synuclein gene having a DNA sequence where a variation (e.g., mutation, etc.,) occurs. Specifically, a gene derived from the α-synuclein gene where a portion of its nucleotide sequence is deleted, a gene derived from the α-synuclein gene where a portion of its nucleotide sequence is substituted by a different nucleotide sequence, a gene derived from the α-synuclein gene where a different nucleotide sequence is inserted to a portion of its nucleotide sequence, or the like, can be used as the variant gene. While the number of nucleotide which is deleted, substituted, or added is not particularly limited, the number is generally approximately 1 to 50, preferably approximately 1 to 15, more preferably approximately 1 to 6. Such deletion, substitution, or addition of the nucleotide sequence brings about the deletion, substitution, or addition of preferably approximately 1 to 5 amino acids, more preferably approximately 1 to 2 amino acids, in the resulting amino acid sequence of α-synuclein. It is preferred to use α-synuclein gene encoding polypeptides having function equal to that of wild-type α-synuclein as these variant genes. The "α-synuclein gene" described herein has the broadest sense that encompasses not only wild-type α-synuclein genes but also all of the variant genes as described above.

Preferably, the α-synuclein gene used in the present invention is a variant α-synuclein gene having a variation that substitutes a different amino acid for an alanine residue at amino acid No. 30 in an amino acid sequence (SEQ ID NO: 16 of the sequence listing) encoded by the wild-type human α-synuclein gene and/or a variation that substitutes a different amino acid for an amino acid residue corresponding to an alanine residue at amino acid No. 53 in the amino acid sequence. The DNA of such a variant α-synuclein gene can be obtained, for example, by PCR using DNA encoding the human α-synuclein gene known in the art as a template and using mutagenic primers that causes missense mutations so that the nucleotides of the α-synuclein gene encoding the alanine residue(s) at amino acid No. 30 and/or amino acid No. 53 in the α-synuclein protein are substituted to encode other amino acids.

In the present invention, a variation that substitutes a proline residue for an alanine residue at amino acid No. 30 in the amino acid sequence described in SEQ ID NO: 16 and a variation that substitutes a threonine residue for an alanine residue at amino acid No. 53 in the amino acid sequence described in SEQ ID NO: 16 are preferred. Of these variations, the latter is particularly preferred. Furthermore, in the present invention, it is preferred to use a gene that is varied from the wild-type α-synuclein gene in a manner that deletes C terminal (1 to 20 amino acid residues from the C terminus, preferably 5 to 15 amino acid residues from the C terminus, e.g., 10 amino acid residues from the C terminus, etc.,) amino acid residues. The use of the variant that is varied in a manner that substitutes a threonine residue for the alanine residue at amino acid residue 53 allows for the reproduction of pathologic states of Parkinson's disease, and the use of the gene that is varied in a manner that deletes the C terminal residues allows for improvement in the expression level of the gene.

Methods such as PCR, primer synthesis, genomic DNA preparation, cloning, and enzyme treatment can be performed by routine methods well known by those skilled in the art.

(2) Generation of Transgenic Non-Human Mammal of the Present Invention

While a generation method of the transgenic non-human mammal of the present invention is not particularly limited, the transgenic non-human mammal can be generated, for example, by introducing an expression vector incorporating the α-synuclein gene therein under the control of a promoter into a fertilized egg or the like. Hereinafter, the generation method of the transgenic non-human mammal that expresses the α-synuclein gene, particularly in neurons as a result of the introduction of the gene, will be described.

It is preferred to use a recombinant gene having the above-described α-synuclein gene inserted distal to an appropriate promoter for mammals as a transgene used for the generation of the transgenic non-human mammal. A poly(A) signal can be inserted downstream of the α-synuclein gene, if desired.

While the type of the promoter for mammals used in the construction of the transgene is not particularly limited, it is preferred to use a promoter capable of expressing the α-synuclein gene in neurons (particularly preferably, in the dopamine neurons). Concrete examples of the promoter capable of driving α-synuclein gene expression in the dopamine neurons include a tyrosine hydroxylase promoter, etc.

Besides, for example, gene promoters derived from viruses (e.g., cytomegalovirus, Moloney leukemia virus, JC virus, mammary tumor virus, etc.,), promoters derived from a variety of mammals (e.g., human, rabbit, dog, cat, guinea pig, hamster, rat, mouse, etc.,) and birds (e.g., chicken, etc.,), and the like, can also appropriately be employed.

Furthermore, the recombinant gene used in the present invention may be ligated with a terminator necessary for α-synuclein gene expression. The terminator is used as a sequence (so-called poly(A)) that terminates transcription of messenger RNA of interest in the transgenic animal, and each gene sequence derived from viruses and from a variety of mammals or birds can be used as the terminator. Specifically, simian virus 40 terminator or the like is used. Besides, the splicing signal and enhancer region of a known gene can be ligated for the purpose of expressing the α-synuclein gene more highly. Furthermore, it is also possible to ligate a portion of the intron of a eukaryotic gene to the 5' upstream region of the promoter region, to between the promoter region and the translated region, or to the 3' downstream region of the translated region.

The α-synuclein gene incorporated in the transgene leads to the intracellular production of α-synuclein, when expressed in the cell such as a fertilized egg.

The transgenic non-human mammal that expresses α-synuclein as a result of the introduction of the α-synuclein gene can be generated, for example, by introducing the α-synuclein gene into the fertilized egg of a non-human mammal, then transplanting the fertilized egg to a pseudopregnant female non-human mammal, and allowing this female non-human mammal to be delivered of a non-human mammal comprising the α-synuclein gene introduced therein.

In addition to rodents such as mice, hamsters, guinea pigs, rats and rabbits, for example, dogs, cats, goats, sheep, cattle, pigs, monkeys, etc., can be used as the non-human mammal. Rodents such as mice, hamsters, guinea pigs, rats, and rabbits are preferred in light of the convenience, etc., of generation, raising, and use. Among these rodents, mice are most preferred.

The transgenic non-human mammal used in the present invention is generated by introducing a recombinant gene containing the foreign α-synuclein gene when the embryonic cell and reproductive or somatic cell of the non-human mammal or an ancestor of this animal are at an embryogenic stage (preferably, introducing the recombinant gene at a single-cell or fertilized egg-cell stage and generally at an 8-cell stage or earlier). The construction of the recombinant gene containing the α-synuclein gene is described above.

The introduction of the α-synuclein gene into the fertilized egg is performed so that the gene is kept present in all of the embryonic cells and somatic cells of the recipient mammal. The presence of the α-synuclein gene in the embryonic cells of the generated animal after gene introduction means that the α-synuclein gene is present in all of the embryonic cells and somatic cells of all the later generations of the generated animal. The progeny of the animal of this species that have inherited genes have the α-synuclein gene in all of their embryonic cells and somatic cells.

The transgenic animal of the present invention can successively be raised as an animal bearing the gene in a usual raising environment, after being confirmed to stably preserve gene by mating. Homozygous animals having the transgene in both homologous chromosomes are obtained, and these male and female homozygotes are mated and thereby, can successively be propagated so that all the progeny have an excess of the gene. Expression of the α-synuclein gene in the transgenic animal can be detected by analyzing its organs, tissues, and cells. Moreover, it is also possible to measure the degree of its expression by enzyme immunoassay using an antibody against α-synuclein.

Hereinafter, a transgenic mouse will be taken as an illustration of the transgenic non-human mammal and described specifically. The transgenic mouse can be generated by the following procedures: a transgene containing α-synuclein-encoding cDNA inserted distal to a promoter is constructed and microinjected into the male pronucleus of a mouse fertilized egg; the obtained egg is cultured and then transplanted into the oviduct of a pseudopregnant female mouse; this recipient animal is then raised to produce mice, from which a mouse having the cDNA is selected. Any of those obtained by the mating of mice derived from, for example, 129/sv, C57BL/6, BALB/c, C3H, SJL/Wt, etc., can be used as the mouse fertilized egg.

Moreover, the suitable number of the transgene to be injected is 100 to 3000 molecules per fertilized egg. Furthermore, the selection of the mouse having the cDNA can be performed by extracting DNA from the mouse tail or the like and subjecting the DNA to a dot hybridization method using a probe corresponding to the introduced α-synuclein gene, or amplifying the DNA by a PCR method using specific primers, or the like.

The transgenic non-human mammal of the present invention, which is characterized by overexpressing α-synuclein, is a model available in a screening test for a therapeutic drug or a preventive drug for Parkinson's disease and is useful in a research field such as the elucidation of mechanisms underlying Parkinson's disease.

Examples of a portion of the transgenic non-human mammal of the present invention include the head, fingers, paws, legs, abdominal regions, tail, etc., of the non-human mammal, in addition to the cell, cell organelle, tissue, and organ of the non-human mammal. All of these portions of the body are encompassed in the scope of the present invention.

(3) Screening of Substance Having Dopamine-Like Action (e.g., Therapeutic Agent and/or Preventive Agent for Parkinson's Disease, etc.,)

A screening method for a substance having dopamine-like action according to the present invention can be performed using the transgenic non-human mammal of the present invention that overexpresses α-synuclein. Namely, a test substance can be evaluated for its therapeutic effect or preventive effect on Parkinson's disease by administering the test substance to the transgenic non-human mammal (e.g., transgenic mouse, etc.,) of the present invention and evaluating and investigating the physiological data, motor ability, and so on, of the transgenic non-human mammal.

Or otherwise, the test substance can also be evaluated for its therapeutic effect or preventive effect on Parkinson's disease by administering the test substance to the transgenic non-human mammal of the present invention and analyzing the expression state or in vivo dynamics of α-synuclein after administration.

Namely, the use of the transgenic non-human mammal of the present invention allows for the evaluation of therapeutic effect and preventive effect on Parkinson's disease. The transgenic non-human mammal of the present invention can be utilized as a model animal for the evaluation of pathologic states of Parkinson's disease. For example, the use of the transgenic non-human mammal of the present invention also makes it possible to assess the degrees of recovery and. severity of these pathologic states and investigate a therapy of this disease.

Furthermore, mechanisms underlying the onset and progression of the disease can be elucidated by analyzing α-synuclein overexpression, the stage of progression of the disease, and so on, with use of the transgenic non-human mammal of the present invention.

Examples of the test substance applied to the screening method of the present invention include peptides, proteins, non-peptidic compounds, synthetic compounds, fermentation products, cell extracts, plant extracts, animal tissue extracts, plasma, etc. These compounds may be novel compounds or may be compounds known in the art. Alternatively, a library containing a plurality of molecules, such as a peptide library and a compound library can also be employed as the test substance.

For example, oral administration, intravenous injection, and so on, are used as methods of administering the test substance to the transgenic non-human mammal of the present invention. Moreover, the dose of the test substance can appropriately be selected according to administration methods, the properties of the test subject, and so on.

A substance obtained using the screening method of the present invention is a substance selected from the test subjects illustrated above. The substance has preventive and therapeutic effects on Parkinson's disease and as such, can be employed as a medicine such as safe and less-toxic therapeutic and preventive agents for Parkinson's disease. Furthermore, a compound derived from the substance obtained by the screening can also be used as such a medicine. The substance obtained by the screening method may form a salt. A salt with a physiologically acceptable acid (e.g., inorganic acid and organic acid) or base (e.g., alkali metal), or the like is used as the salt of the substance. Among others, a physiologically acceptable acid-addition salt is preferred.

For example, a salt with an inorganic acid (e.g., hydrochloric acid, phosphoric acid, hydrobromic acid, and sulfuric acid) or a salt with an organic acid (e.g., acetic acid, formic acid, propionic acid, fumaric acid, maleic acid, succinic acid, tartaric acid, citric acid, malic acid, oxalic acid, benzoic acid, methanesulfonic acid, and benzenesulfonic acid), or the like is used as the salt.

For example, the substance obtained by the screening method can be used orally in the form of a tablet (if necessary, coated with sugar), capsule, elixir, microcapsule, or the like, or can be used parenterally in the form of a sterile solution or an injection such as a suspension, with water or other pharmacologically acceptable liquids.

A preparation can be produced, for example, by mixing the substance together with a physiologically acceptable carrier, flavoring agent, excipient, vehicle, antiseptic, stabilizer, binder, and so on. For example, a binder such as gelatin, corn starch, tragacanth, or gum arabic, an excipient such as crystalline cellulose, a swelling agent such as corn starch, gelatin, or alginic acid, a lubricant such as magnesium stearate, a sweetening agent such as sucrose, lactose, or saccharine, a flavoring agent such as peppermint, *Gaultheria adenothrix* oil, or cherry, and the like, are used as additives that can be mixed into a tablet, capsule, and so on. A sterile composition for injection can be formulated according to a routine method such as the dissolution or suspension of an active substance in a vehicle such as water for injection, naturally produced plant oil such as sesame oil and coconut oil, or the like. For example, an isotonic solution or the like (e.g., D-sorbitol, D-mannitol, sodium chloride, etc.,) containing physiological saline, glucose, and other adjuvants is used as an aqueous solution for injection and can also be used in combination with appropriate solubilizing agents, for example, alcohol (e.g., ethanol), polyalcohol (e.g., propylene glycol and polyethylene glycol), a non-ionic surfactant (e.g., Polysorbate 80™ and HCO-50), and so on. For example, sesame oil, soybean oil, or the like is used as an oily solution for injection and may also be used in combination with a solubilizing agent such as benzyl benzoate and benzyl alcohol.

Moreover, the therapeutic agent and/or preventive agent for Parkinson's disease may also be supplemented with, for example, a buffer (e.g., phosphate buffer and sodium acetate buffer), a soothing agent (e.g., benzalkonium chloride and procaine hydrochloride), a stabilizer (e.g., human serum albumin, polyethylene glycol, etc.,), a preservative (e.g., benzyl alcohol, phenol, etc.,), an antioxidant, and so on.

The preparation thus obtained is safe and less toxic and as such, can be administered to, for example, humans and other mammals. While the dose of the substance differs depending on target disease, recipients, administration routes, and so on, the dose of the compound, for example when orally administered, is generally approximately 0.1 to 100 mg, preferably approximately 1.0 to 50 mg per day, for an adult. For example, when the compound is parenterally administered, the single dose of the compound differs depending on recipients, target disease, and so on. The dose of the compound, for example when administered in the form of an injection to an ordinary adult, is approximately 0.01 to 100 mg, preferably approximately 0.1 to 50 mg per day, through intravenous injection.

Hereinafter, the present invention will be described more fully with reference to Examples. However, the present invention is not intended to be limited to Examples.

EXAMPLES

Example 1

Cloning of a Human α-Synuclein Gene

Human brain-derived cDNA (manufactured by Clontech) was used as a template to amplify a human α-synuclein gene by PCR using oligonucleotides of Sequence-1 and Sequence-2 as primers. A kit manufactured by Takara Bio (Takara LA PCR Kit Ver. 2) and PCR Thermal Cycler MP (manufactured by Takara Bio) were used for PCR.

Composition of Reaction Solution

| Human brain-derived cDNA | 1 µl |
|---|---|
| 10x PCR buffer solution | 5 µl |
| 2.5 mM dNTP | 4 µl |
| 10 µM oligonucleotide (Sequence-1) | 2 µl |
| 10 µM oligonucleotide (Sequence-2) | 2 µl |
| Water | 35.5 µl |
| LA Taq Polymerase | 0.5 µl |
| Total: | 50 µl |

Reaction Conditions

The reaction solution was first maintained at 94° C. for 2 minutes, then reacted at 94° C. for 30 seconds, and cooled to 60° C. and kept at 60° C. for 1 minute and further at 72° C. for 3 minutes. This cycle was repeated 30 times to amplify the sequence of interest.

```
Sequence-1:
GGAATTCATTAGCCATGGATGTATTC    (SEQ ID NO: 1)

Sequence-2:
AGCCACTTAAGGAACCAGTGCATACC    (SEQ ID NO: 2)
```

The amplified DNA fragments were fractionated by agarose gel electrophoresis (gel concentration: 1%), and a band (1.24 kb) containing the human α-synuclein gene was excised according to a routine method. The extraction and purification of the DNA fragment from the agarose gel were performed using GENECLEAN II Kit (manufactured by Bio 101). This purified DNA fragment was inserted into pT7Blue T-Vector (manufactured by Novagen), a vector for sequencing, by a method described below. A kit manufactured by Takara Bio (TaKaRa DNA Ligation Kit Ver. 2) was used as a ligation solution to perform reaction at 16° C. for 1.5 hours.

Composition of Reaction Solution

| PCR product | 1 µl (50 ng) |
|---|---|
| T7 Blue T-vector | 1 µl (17 ng) |
| Water | 3 µl |
| Ligation solution | 5 µl |
| Total: | 10 µl |

The resulting reaction solution was used to perform the transformation of *E. coli* K12 strain DH5 according to a routine method. The resulting transformant was plated to an LB agar medium containing 50 µg/ml ampicillin (Amp) and cultured overnight at 37° C. The colonies were inoculated into 10 ml of LB liquid medium containing 50 µg/ml Amp and cultured overnight at 37° C. After the bacterial cells were collected by centrifugation, recombinant DNA was purified using QIAprep Spin Plasmid Miniprep Kit (manufactured by QIAGEN), and the whole nucleotide sequence thereof was determined according to a routine method. The nucleotide sequence was identical to the sequence (Accession No: L08850) registered in GenBank. The recombinant DNA thus constructed was designated as pT7NACP140.

Example 2

Preparation of Variant Human α-Synuclein Gene

The pT7NACP140 was used as a template to introduce a point mutation using TaKaRa LA PCR in vitro Mutagenesis Kit (manufactured by Takara Bio) in a manner that would change alanine (codon: GCA) at residue 53 to threonine (codon: ACA).

Composition of Reaction Solution

| pT7NACP140 | 1 µl (1 ng) |
|---|---|
| 10 µM oligonucleotide (Sequence-3 or -5) | 2 µl |
| 10 µM oligonucleotide (Sequence-4 or -6) | 2 µl |
| 10x PCR buffer solution | 5 µl |
| 2.5 mM dNTP | 4 µl |
| Water | 35.5 µl |
| LA Taq Polymerase | 0.5 µl |
| Total: | 50 µl |

Reaction Conditions

The reaction solution was first maintained at 94° C. for 2 minutes, then reacted at 94° C. for 30 seconds, and cooled to 60° C. and kept at 60° C. for 2 minutes and further at 72° C. for 3 minutes. This cycle was repeated 25 times to amplify the sequence of interest.

```
Sequence-3:
AGCTCTAATACGACTCACTATAGGG    (SEQ ID NO: 3)

Sequence-4:
CAGCCACTGTTGCCACACCATGC      (SEQ ID NO: 4)
```

-continued

```
Sequence-5:
AGGGTTTTCCCAGTCACGACGTTG        (SEQ ID NO: 5)

Sequence-6:
GCATGGTGTGGCAACAGTGGCTG         (SEQ ID NO: 6)
```

The PCR product obtained using Sequence-3 and Sequence-4 and the PCR product obtained using Sequence-5 and Sequence-6 were mixed in equal amounts. The resulting mixture was heated at 94° C. for 10 minutes, then cooled to 37° C. over 60 minutes, and kept at 37° C. for 15 minutes. PCR reaction was performed using this reaction solution as a temple to amplify the DNA having the point mutation of interest introduced therein.

Composition of Reaction Solution

| | |
|---|---|
| Mixture solution | 1 µl |
| 10 µM oligonucleotide (Sequence-3) | 2 µl |
| 10 µM oligonucleotide (Sequence-5) | 2 µl |
| 10x PCR buffer solution | 5 µl |
| 2.5 mM dNTP | 4 µl |
| Water | 35.5 µl |
| LA Taq Polymerase | 0.5 µl |
| Total: | 50 µl |

Reaction Conditions

The reaction solution was first maintained at 94° C. for 2 minutes, then reacted at 94° C. for 30 seconds, and cooled to 60° C. and kept at 60° C. for 2 minutes and further at 72° C. for 3 minutes. This cycle was repeated 25 times to amplify the sequence of interest.

The amplified DNA fragment was purified using the same method as described in Example 1 and inserted into pT7Blue T-Vector (manufactured by Novagen). The recombinant DNA thus constructed was designated as pT7NACP140m. The entire nucleotide sequence of a region containing the human α-synuclein gene was determined according to a routine method to confirm that the desired point mutation was successfully introduced into the gene.

The pT7NACP140m was used as a template to amplify a region from the initiation codon to the codon at residue 130 inclusive for the human α-synuclein protein by PCR using oligonucleotides of Sequence-1 and Sequence-7 as primers. The oligonucleotide of Sequence-7 was designed to provide a termination codon immediately after the codon at residue 130. Moreover, PCR was performed using Pfu DNA Polymerase (manufactured by Stratagene) so as not to introduce new mutations during DNA amplification.

Composition of Reaction Solution

| | |
|---|---|
| pT7NACP140m | 1 µl (10 ng) |
| 10x PCR buffer solution | 5 µl |
| 2.5 mM dNTP | 4 µl |
| 10 µM oligonucleotide (Sequence-1) | 2 µl |
| 10 µM oligonucleotide (Sequence-7) | 2 µl |
| Water | 35.5 µl |
| Pfu DNA Polymerase | 0.5 µl |
| Total: | 50 µl |

Reaction Conditions

The reaction solution was first maintained at 94° C. for 2 minutes, then reacted at 94° C. for 30 seconds, and cooled to 60° C. and kept at 60° C. for 1 minute and further at 72° C. for 3 minutes. This cycle was repeated 30 times to amplify the sequence of interest.

```
Sequence-7:
TAGCCTTAAGTTACTCAGAAGGCATTT     (SEQ ID NO: 7)
```

The obtained DNA fragment was inserted into pCR-Blunt (manufactured by Invitrogen) using the same method as described in Example 1. The recombinant DNA thus constructed was designated as pCRNACP130m. The entire nucleotide sequence of a region containing the variant human α-synuclein gene was determined according to a routine method to confirm that the recombinant DNA had the desired sequence.

Example 3

Preparation of DNA Fragment for Microinjection

The pCRNACP130m was cleaved with PstI and SpeI. The cleaved fragments were fractionated by agarose gel electrophoresis (gel concentration: 1%), and a band (417 bp) containing the variant human α-synuclein gene was excised according to a routine method. The extraction and purification of the DNA fragment from the agarose gel were performed using GENECLEAN II Kit (manufactured by Bio 101). Additionally, both ends of the DNA fragment were blunt-ended according to a routine method. Subsequently, a pTH/-9 kb expression vector having a rat tyrosine hydroxylase gene promoter (Iwawaki, T. et al., Biochem Biophys Res Commun 274, 590-595 (2000)) was cleaved with XhoI and HindIII. The resulting fragment having the promoter was inserted into pBST-N (Kobayashi, K. et al., Proc Natl Acad Sci USA 89, 1631-1635 (1992)) to prepare pRTH-BstN. The pRTH-BstN was cleaved with EcoRI, and both ends thereof were blunt-ended and then dephosphorylated according to a routine method. This vector was mixed with the fragment containing the variant human α-synuclein gene. Ligation was performed using the same method as described in Example 1, and the transformation of E. coli K12 strain DH5 was performed, and recombinant DNA was prepared form the transformant. The recombinant DNA thus constructed was designated as pRTHNACP130m. The pRTHNACP130m was cleaved with SalI. The cleaved fragments were fractionated by agarose gel electrophoresis (gel concentration: 0.8%), and a band (11.4 kb) of interest was excised according to a routine method. The extraction and purification of the DNA fragment from the agarose gel were performed using GENECLEAN II Kit (manufactured by Bio 101). The purified DNA fragment was dissolved at the final concentration of 12.6 ng/µl (=2000 copies/2 pl) in Dulbecco's phosphate buffered solution (manufactured by Invitrogen), and this solution was used as a DNA solution for microinjection.

Example 4

Construction of Variant Human α-Synuclein Transgenic Mouse

Frozen pronuclear-stage eggs of the B6C3F1 lineage (purchased from CHARLES RIVER LABORATORIES JAPAN) were thawed using the method recommended by CHARLES RIVER LABORATORIES JAPAN. Namely, a cryotube (12 mm in diameter, 40 mm in length; manufactured by Nalgenunc) accommodating the frozen pronuclear-stage eggs was removed from liquid nitrogen and left at room temperature (23° C.) for 1 minute. To the cryotube, 900 µl of 0.25 M sucrose solution for mouse embryos (manufactured by Dia-Iatron) heated to 37° C. was added, and the frozen materials was quickly thawed by pipetting. The resulting thawed suspension was transferred to a plastic petri dish of 35 mm in diameter to collect the pronuclear-stage eggs using a capillary for embryo handling. The pronuclear-stage eggs were washed 3 times with a PB1 buffer solution and then cultured (37° C., 5% $CO_2$) for 1 hour in an mW medium for mouse embryos (manufactured by Mitsubishi Kagaku Iatron).

Composition of PB1 Buffer Solution (g/100 ml of Sterile Distilled Water)

| | |
|---|---|
| NaCl | 0.8 |
| KCl | 0.02 |
| $CaCl_2$ | 0.012 |
| $KH_2PO_4$ | 0.02 |
| $MgCl \cdot 6H_2O$ | 0.01 |
| $Na_2HPO_4$ | 0.115 |
| Sodium pyruvate | 0.0036 |
| Glucose | 0.1 |
| Penicillin G Potassium Meiji (manufactured by Meiji Seika) | 0.0075 |
| Albumin Fraction V Powder (manufactured by Sigma) | 0.3 |

An microinjection apparatus (inverted microscope TE300 (manufactured by Nikon) equipped with a Nomarski differential interferometer and installed with a micromanipulator MMO-204 (manufactured by Narishige), a microinjector IM-50A/B (manufactured by Narishige), and a microsyringe (manufactured by Hamilton)) was used to inject 2 pl (2000 copies) of the DNA solution prepared in Example 3 into the male pronuclei of the pronuclear-stage eggs according to a routine method. A microcapillary for fertilized egg holding and a microcapillary for DNA injection were made by processing borosilicate glass tubes (10 cm in length, 1.0 mm in diameter, 0.75 mm in interior diameter; manufactured by Sutter) with a puller P-97/IVF (manufactured by Sutter) and a microforge MF-900 (manufactured by Narishige). A micro cover glass (manufactured by Matsunami Glass) to which Swinnex Gasket 015 (manufactured by Millipore) was affixed was used as a slide glass for DNA injection procedures.

After DNA injection, the pronuclear-stage eggs were cultured (37° C., 5% $CO_2$) overnight in an mW medium for mouse embryos (manufactured by Mitsubishi Kagaku Iatron). Next morning, the developed 2-cell-stage embryos were transplanted according to a routine method into the ampullae of the oviducts of pseudopregnant recipient mice (ICR lineage, female, 8 weeks of age; purchased from Japan SLC) that had been mated with vasoligated male mice (10 weeks of age; purchased from Japan SLC) of the same lineage. After 19 days from the transplantation, the recipient mice were subjected to cesarean section to extract mice derived from the transplanted embryos. The mice were raised until weaning by a foster mother (12-week-old female mouse of the ICR lineage after 1 day from childbirth; purchased from Japan SLC). After 28 days from the cesarean section, the mice were weaned from the breast and used as founder mice.

Example 5

Selection of Variant Human α-Synuclein Transgenic Mouse

After 5-mm tail tips were excised from the weaned mice under anesthesia with diethyl ether, the individuals were identified by an ear punching method. The collected tails were immersed and shaken overnight at 55° C. in 400 µl of DNA extraction buffer solution (100 mM NaCl, 50 mM Tris-HCl (pH 7.5), 20 mM EDTA, and 1% SDS) supplemented with 20 µl of 20 mg/ml proteinase K (manufactured by Takara Bio). A 1-µl aliquot of the lysate was diluted 100-fold with sterile distilled water and used as sample DNA. Oligonucleotides of Sequence-8 and Sequence-9 having a partial sequence of the introduced DNA and oligonucleotides of Sequence-10 and Sequence-11 for an internal standard having a partial sequence of an acetylcholine receptor protein Rapsyn were used as primers to perform PCR. TaKaRa LA Taq™ (manufactured by Takara Bio) and Gene Amp PCR System 9700 (manufactured by Applied Bio Systems Japan) were used for PCR.

```
Sequence-8:
GTGGCTGCTGCTGAGAAAAC            (SEQ ID NO: 8)

Sequence-9:
GTGGGGCTCCTTCTTCATTC            (SEQ ID NO: 9)

Sequence-10:
AGGACTGGGTGGCTTCCAACTCCCAGACAC  (SEQ ID NO: 10)

Sequence-11:
AGCTTCTCATTGCTGCGCGCCAGGTTCAGG  (SEQ ID NO: 11)
```

Composition of Reaction Solution

| | |
|---|---|
| Sample DNA | 1 µl |
| 10 µM oligonucleotide (Sequence-8) | 1 µl |
| 10 µM oligonucleotide (Sequence-9) | 1 µl |
| 10 µM oligonucleotide (Sequence-10) | 1 µl |
| 10 µM oligonucleotide (Sequence-11) | 1 µl |
| 10x PCR buffer solution | 2.5 µl |
| 25 mM $MgCl_2$ | 1.5 µl |
| 2.5 mM dNTP | 2 µl |
| Water | 13.75 µl |
| LA Taq Polymerase | 0.25 µl |
| Total: | 25 µl |

As PCR conditions, the reaction solution was maintained at 94° C. for 9 minutes and then reacted at 94° C. for 1 minute, then at 60° C. for 1 minute, and further at 72° C. for 2 minutes. This cycle was repeated 5 times, and an additional reaction cycle of 94° C. for 1 minute, 60° C. for 1 minute, and 72° C. for 1 minute was repeated 28 times to amplify the sequence of interest. The amplified DNA was electrophoresed for 40 minutes at 100 V on 2% TAE agarose (Seakem ME Agarose; manufactured by Takara Bio) gel according to a routine method. The gel was stained with an ethidium bromide solution (manufactured by Amersham Biosciences), followed by ultraviolet irradiation to select, as Tg animals, individuals having both of a DNA fragment (279 bp) amplified with Sequence-8 and Sequence-9 and a DNA fragment (591 bp) amplified with Sequence-10 and Sequence-11 (FIG. 1).

Example 6

Breeding of Variant Human α-Synuclein Transgenic Mouse

Transgene-positive individuals were obtained by analyzing the founder mice obtained in Example 4 by the method described in Example 5. The individuals were mated with mice of the C57B6/J lineage (purchased from CLEA Japan) to produce F1 generations. Backcross with the mice of the C57B6/J lineage was further repeated to produce N2 to N6 generations. The gene analysis of the F1 generations was performed by Southern hybridization described in Example 7 to estimate a copy number of the gene incorporated into the chromosomes. For the founder mouse shown by this analysis to comprise the transgene inserted into several sites of the chromosome, individual lines of the respective inserted sites were established at the step of the backcross with the mice of the C57B6/J lineage. A total of 9 founder mice were constructed by these procedures, from which variant human α-synuclein transgenic mice of 12 lines in total were in turn established.

Example 7

Southern Hybridization Analysis

A digoxigenin-labeled probe specific to the variant human α-synuclein gene was prepared by a method described below. At first, oligonucleotides of Sequence-12 and Sequence-13 having a sequence complementary to a portion of the variant human α-synuclein gene were used as primers to perform PCR using the pRTHNACP130m prepared in Example 3 as a template. Ampli Taq Gold (manufactured by Roche Diagnostics) and TaKaRa PCR Thermal Cycler MP (manufactured by Takara Bio) were used for PCR.

```
Sequence-12:
GTGGCTGCTGCTGAGAAAAC        (SEQ ID NO: 12)

Sequence-13:
GTGGGGCTCCTTCTTCATTC        (SEQ ID NO: 13)
```

Composition of Reaction Solution

| | |
|---|---|
| pRTHNACP130m (10 pg/μl) | 1 μl |
| 10x PCR buffer (manufactured by Roche Diagnostics) | 2.5 μl |
| Gene Amp dNTP Mix (manufactured by Roche Diagnostics) | 1.5 μl |
| 10 μM oligonucleotide (Sequence-12) | 1 μl |
| 10 μM oligonucleotide (Sequence-13) | 1 μl |
| Sterile distilled water | 17.75 μl |
| 5 U/μl Ampli Taq Gold (manufactured by Roche Diagnostics) | 0.25 μl |
| Total: | 25 μl |

Reaction Conditions

The reaction solution was first maintained at 94° C. for 9 minutes and then reacted at 94° C. for 1 minute, then at 60° C. for 1 minute, and further at 72° C. for 2 minutes. This cycle was repeated 5 times, and an additional reaction cycle of 94° C. for 1 minute, 60° C. for 1 minute, and 72° C. for 1 minute was repeated 28 times to amplify the sequence of interest.

After the completion of the reaction, a 3-μl aliquot was collected from the solution and fractionated by 1.2% agarose gel electrophoresis according to a routine method to investigate an electrophoresis image. This electrophoresis image showed that the 279-bp DNA fragment having a partial sequence of the variant human α-synuclein gene was specifically amplified. Then, PCR DIG Probe Synthesis Kit (manufactured by Roche Diagnostics) was used to perform the digoxigenin labeling of this DNA fragment. TaKaRa PCR Thermal Cycler MP was used for the reaction.

Composition of Reaction Solution

| | |
|---|---|
| Solution of the above-described PCR diluted 100-fold with sterile distilled water | 1 μl |
| 10-fold concentration of MgCl$_2$-containing PCR buffer (manufactured by Roche Diagnostics) | 5 μl |
| 10-fold concentrated PCR DIG Mix (manufactured by Roche Diagnostics) | 5 μl |
| 10 μM oligonucleotide (Sequence-12) | 1 μl |
| 10 μM oligonucleotide (Sequence-13) | 1 μl |
| Sterile distilled water | 36.25 μl |
| Expand High Fidelity (manufactured by Roche Diagnostics) | 0.75 μl |
| Total: | 50 μl |

Reaction Conditions

The reaction solution was first maintained at 95° C. for 2 minutes and then reacted at 95° C. for 1 minute, then at 60° C. for 1 minute, and further at 72° C. for 2 minutes. This cycle was repeated 10 times, and an additional reaction cycle of 95° C. for 1 minute, 60° C. for 1 minute, and 72° C. for 1 minute was repeated 35 times. By these procedures, the sequence of interest was amplified, while digoxigenin labeling was performed by incorporating DIG-dUTP into the PCR product.

After the completion of the reaction, a 3-μl aliquot was collected from the solution and fractionated by 1.2% agarose gel electrophoresis according to a routine method. The digoxigenin labeling was confirmed by the shift of the original 279-bp band to a band of higher molecular weight.

Next, tail tissue-derived DNA was prepared by a method described below. The tail biopsy (5 mm) was placed in a 2-ml Eppendorf tube, to which 400 μl of Buffer ATL (manufactured by QIAGEN) and 20 μl of Proteinase K Solution (manufactured by QIAGEN) were then added, followed by immersion and shaking overnight at 55° C. The resulting lysate was centrifuged at room temperature (23° C.) for 10 minutes at 15000×g to separate a supernatant from a pellet. A 300-μl aliquot of the supernatant was collected, and DNA was purified therefrom using an automatic nucleic acid isolator PT-200 (manufactured by Kurabo). Then, the concentration of the DNA was quantified using a spectrophotometer DU-640 (manufactured by Beckman). The tail tissue-derived DNA (10 μg) was treated with EcoRI. The treated fragments were fractionated by 1.2% agarose gel electrophoresis according to a routine method and transferred to a nylon membrane plus charge (manufactured by Roche Diagnostics). The membrane was placed in Hybri-Bag (manufactured by Cosmo Bio), to which 20 ml of DIG Easy Hyb (manufactured by Roche Diagnostics) was then added, followed by immersion and shaking at 42° C. for 30 minutes. The probe specific to the variant human α-synuclein gene (rapidly cooled on ice immediately after being heated at 100° C. for 10 minutes) was diluted at the final concentration of 50 ng/ml with 20 ml DIG Easy Hyb, and the DIG Easy Hyb in the Hybri-Bag was replaced with the probe solution. After the membrane was immersed and shaken at 42° C. for 12 hours, the membrane was treated with 2×SSC (0.1% SDS) at 42° C. for 10 minutes and subsequently with 0.1×SSC (0.1% SDS) at 65° C. for 40 minutes. The detection of the digoxigenin-labeled probe specifically bound to the membrane was performed using DIG Wash and Block Buffer Set (manufactured by Roche Diagnostics). Namely, the membrane was immersed in a blocking solution (manufactured by Roche Diagnostics) diluted 2-fold with a maleic acid buffer (manufactured by Roche Diagnostics), and shaken at room temperature (23° C.) for 2 hours. Next, an alkaline phosphatase-labeled anti-digoxigenin Fab fragment (manufactured by Roche Diagnostics) was diluted 10000-fold with this solution, and the membrane was immersed and shaken therein for 30 minutes. After the membrane was further washed for 40 minutes with a wash buffer (manufactured by Roche Diagnostics), CDP-Star (manufactured by Roche Diagnostics) was diluted 100-fold with a detection buffer (manufactured by Roche Diagnostics) and reacted with the membrane. Lumi-Imager F1 WorkStation (manufactured by Roche Diagnostics) was used for signal detection.

Figure 2:
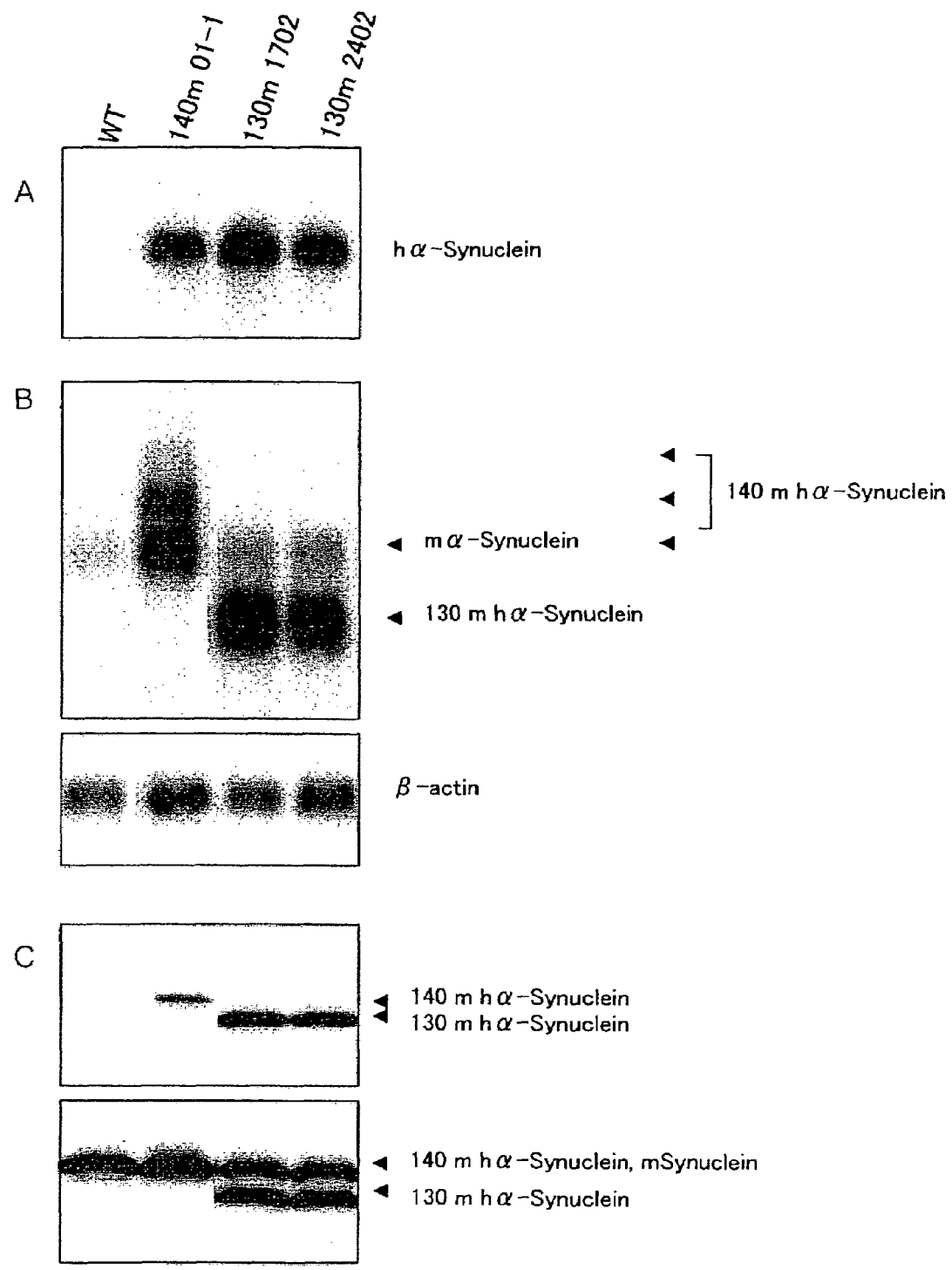
FIG. 2 shows a result of gene expression analysis.

As a result of Southern hybridization analysis, a 346-bp band derived from the transgene was detected in the transgenic mice, but not in wild-type mice (FIG. 2A). The signal intensity of the band largely differed among the lines. When the inserted copy number in each line was estimated from the signal intensity, the line (1702 line) having the highest copy number was considered to comprise approximately 30 copies of the transgene inserted therein.

The fertilized egg (mark to provide identification: TH/syn130m1702) of the constructed transgenic mouse (1702 line) was deposited as deposition No. FERM P-19546 in International Patent Organism Depositary, the National Institute of Advanced Industrial Science and Technology (Tsukuba Central 6, 1-1-1 Higashi, Tsukuba, Ibaraki, Japan) on Oct. 2, 2003, and transferred as deposition No. FERM BP-10131 to international deposition on Sept. 16, 2004.

Mice derived from this cell express human α-synuclein gene variants in the dopamine neurons. Similarly, the fertilized egg (mark to provide identification: TH/syn130m Tg2402) of the constructed transgenic mouse (2402 line) was deposited as deposition No. FERM P-19733 in International Patent Organism Depositary, the National Institute of Advanced Industrial Science and Technology (Tsukuba Central 6, 1-1-1 Higashi, Tsukuba, Ibaraki, Japan) on Mar. 12, 2004, and transferred as deposition No. FERM BP-10132 to international deposition on Sep. 16, 2004. Mice derived from this cell express human α-synuclein gene variants in the dopamine neurons.

Example 8

Northern Hybridization Analysis

Mouse brain tissues were collected and placed into a cryotube (12 mm in diameter, 40 mm in length; manufactured by Nalgenunc), and quickly frozen in liquid nitrogen. The frozen brain tissues were placed in a deep freezer (manufactured by Sanyo) and stored at −80° C. until RNA was extracted. Total RNA extraction was performed using ISOGEN (manufactured by Nippon Gene) according to the method recommended by Nippon Gene. Namely, the frozen brain tissues were hammered and broken into pieces while being immersed in liquid nitrogen. A 100-mg aliquot of the broken pieces was measured and placed into an 2-ml Eppendorf tube. To the tube, 1 ml of ISOGEN was added, and the resulting mixture was homogenized for 20 seconds with a homogenizer (manufactured by Hitachi). The tube was left undisturbed at room temperature (23° C.) for 5 minutes and then supplemented with 200 µl of chloroform, followed by vigorous stirring for 2 minutes. The tube was left undisturbed for 3 minutes and then centrifuged at 4° C. for 15 minutes at 12000×g to collect 600 µl of a supernatant. This supernatant was supplemented with 500 µl of isopropanol and left undisturbed for 10 minutes. The mixture was centrifuged at 4° C. for 10 minutes at 12000×g, and a pellet was washed with 70% ethanol. The washed pellet was dissolved in 300 µl of diethyl pyrocarbonate-treated water, and the RNA concentration was quantified using a spectrophotometer DU-640 (manufactured by Beckman).

Preparation of poly(A) $^+$RNA from the total RNA was performed using Oligotex-dT30 Super (manufactured by Roche Diagnostics) according to the method recommended by Roche Diagnostics. Namely, 200 µg of the total RNA was adjusted to the total volume of 200 µl by adding Elution Buffer (10 mM Tris-HCl (pH 7.5), 1 mM EDTA, and 0.1% SDS) thereto. The resulting solution was supplemented with 200 µl of Oligotex-dT30 Super, then heated at 65° C. for 5 minutes, and rapidly cooled on ice for 3 minutes. The suspension was supplemented with 40 µl of 5 M NaCl and incubated at 37° C. for 10 minutes. The mixture was centrifuged at 4° C. for 3 minutes at 15000×g to remove a supernatant. A pellet was suspended in 500 µl of Washing Buffer (10 mM Tris-HCl (pH 7.5), 1 mM EDTA, 0.5 M NaCl, and 0.1% SDS). The suspension was centrifuged at 4° C. for 3 minutes at 15000×g to remove a supernatant. A pellet was suspended in 200 µl of diethyl pyrocarbonate-treated water, then heated at 65° C. for 5 minutes, and rapidly cooled on ice for 3 minutes. The suspension was centrifuged at 4° C. for 3 minutes at 15000×g to collect poly(A) $^+$RNA in a supernatant.

A 5-µg aliquot of the poly(A) $^+$RNA was fractionated by 1.0% denaturing agarose gel electrophoresis according to a routine method and transferred to a nylon membrane plus charge (manufactured by Roche Diagnostics). The detection of the transgene MRNA was performed in the same way as in Example 7. After detection, the probe was removed by heating the membrane at 100° C. for 10 minutes in 0.5% SDS. Next, for the purpose of correcting the amount of the poly(A) $^+$RNA applied to each lane, the same membrane was used to perform hybridization using the cDNA fragment of digoxigenin-labeled β-actin as a probe. Hybridization conditions were the same as in the method described above. The digoxigenin-labeled cDNA fragment of β-actin was prepared using mouse brain-derived cDNA as a template and oligonucleotides of Sequence-14 and Sequence-15 as primers by using the same method as described above.

```
Sequence-14:
TGTGATGGTGGGAATGGGTCAG        (SEQ ID NO: 14)

Sequence-15:
TTTGATGTCACGCACCATTTCC        (SEQ ID NO: 15)
```

As a result of the Northern hybridization, the expression of not only the foreign human α-synuclein gene but also a mouse endogenous α-synuclein gene was detected by the probe specific to the variant human α-synuclein gene. The MRNA for the former was detected as a band of approximately 1.0 kb, and the mRNA for the latter was detected as a band of approximately 1.6 kb. A human α-synuclein gene expression level largely differed among the lines and strongly correlated with the inserted copy number of the transgene estimated by Southern hybridization. Namely, the expression level was highest in the 1702 line which was estimated to have the highest inserted copy number (approximately 30 copies) (FIG. 2B). Likewise, the expression level in the 2402 line was also high (FIG. 2B).

Example 9

Western Blotting Analysis

Mouse brain tissues were individually immersed in a 20-fold volume of TBS buffer (20 mM Tris-HCl (pH 8.0) and 150 mM NaCl having protease inhibitor Complete Mini (manufactured by Roche Diagnostics) and 1% phosphatase inhibitor cocktail I (manufactured by Sigma) dissolved therein) and homogenized with a homogenizer (manufactured by Hitachi). The homogenates were further sonicated with a sonicator (manufactured by TAITEC), and the obtained lysates were centrifuged at 4° C. for 3 minutes at 2500 rpm. Supernatants were collected and further centrifuged at 4° C. for 1 hour at 45000 rpm. Protein concentrations in the supernatants were measured using Bicucullic Acid (BCA) Protein Assay (manufactured by Pierce).

These proteins were electrophoresed and fractionated on SDS-polyacrylamide gel (manufactured by TEFCO) and transferred to a PVDF membrane (manufactured by Amersham Biosciences) under semi-dry conditions at 2 mA/cm$^2$ for 120 minutes. While 16% gel was used in the detection of variant human α-synuclein, 10% gel was used in the detection of tyrosine hydroxylase. After transfer, the PVDF membrane was blocked overnight at 4° C. in a TBS solution containing 5% skim milk. NACP-5 (Wakabayashi, K. et al. Acta Neuropathol (Berl) 99, 14-20 (2000)), an α-synuclein protein-specific antibody, was used as a primary antibody for detecting the human and mouse α-synuclein proteins. The NACP-5 was diluted 5000-fold with TBS containing 0.5% skim milk and then used. An anti-tyrosine hydroxylase polyclonal antibody (manufactured by Novus Biologicals) was diluted 400-fold in the same way and used in the detection of tyrosine hydroxylase. HRP-labeled anti-rabbit IgG (manufactured by Amersham Biosciences) was diluted 1000-fold in the same way and used as a secondary antibody. The detection was performed with ECL Western blotting detection reagents (manufactured by Amersham Biosciences) as substrates, by exposing the membrane to Hyper film ECL (manufactured by Amersham Biosciences) and measuring the intensity of a band by ImageMaster 1D Elite.

The variant human α-synuclein protein whose C-terminal 10 residues were deleted was detected as a band of approximately 18 kDa, that has a lower molecular weight than that of mouse endogenous α-synuclein (molecular weight of approximately 19 kDa in electrophoresis). Therefore, the same membrane was used to allow for the comparative quantification of expression levels of the foreign and endogenous α-synuclein proteins. The 1702 line having the highest gene expression level was confirmed to express human α-synuclein approximately 3 times (at the corpus striatum site) and approximately twice (at the midbrain site) as much as endogenous α-synuclein (FIG. 2C). Likewise, the 2402 line was also confirmed to express human α-synuclein at a higher expression level as compared with the expression level of endogenous α-synuclein (FIG. 2C).

Figure 3:
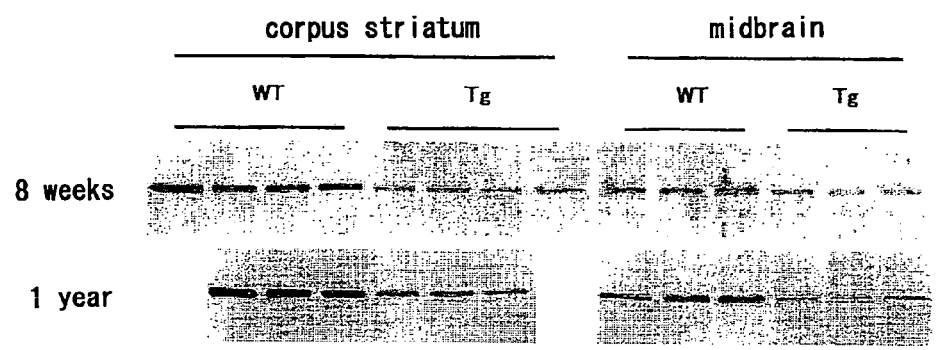
FIG. 3 shows a result of the quantification of tyrosine hydroxylase protein levels in the corpus striatum by Western blotting.
Figure 3:
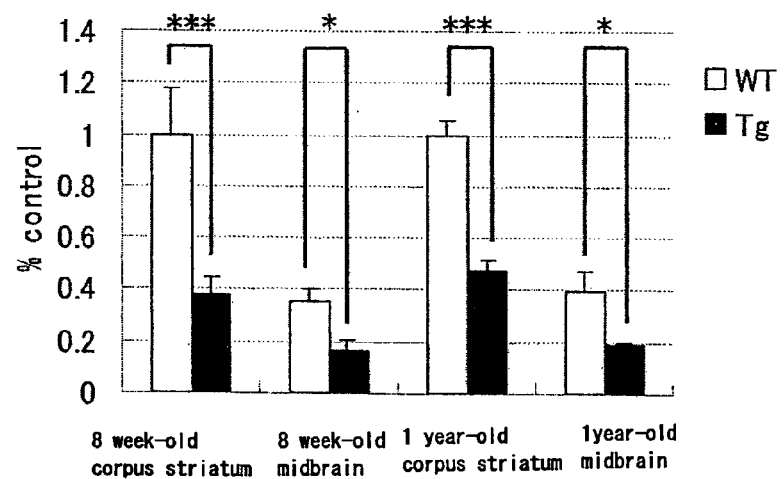

The tyrosine hydroxylase protein was detected as a band of approximately 56-kDa. In the 1702 line having the highest α-synuclein expression level, its tyrosine hydroxylase protein levels in the corpus striata at 8 weeks of age and at 1 year of age were significantly decreased to 40% and 60%, respectively, as compared with those of wild-type mice (FIG. 3).

Example 10

Surface Righting Reflex Test

The 3-day-old to 14-day-old mice were used as subjects and laid on their backs on filter papers. Time required to return to the normal position was measured. The time was measured down to 0.1 seconds using a stop watch (Time Keeper; manufactured by Seiko). Limit of observation time was set to 30 seconds. When reflex was not observed within the limit observation time, reflex latency was defined as 30 seconds. The test was conducted 3 times everyday during a time period from 1 p.m. to 2 p.m, and the median thereof was used as a raw score. Statistical analysis was performed using Mann-Whitney's U test.

Figure 4:
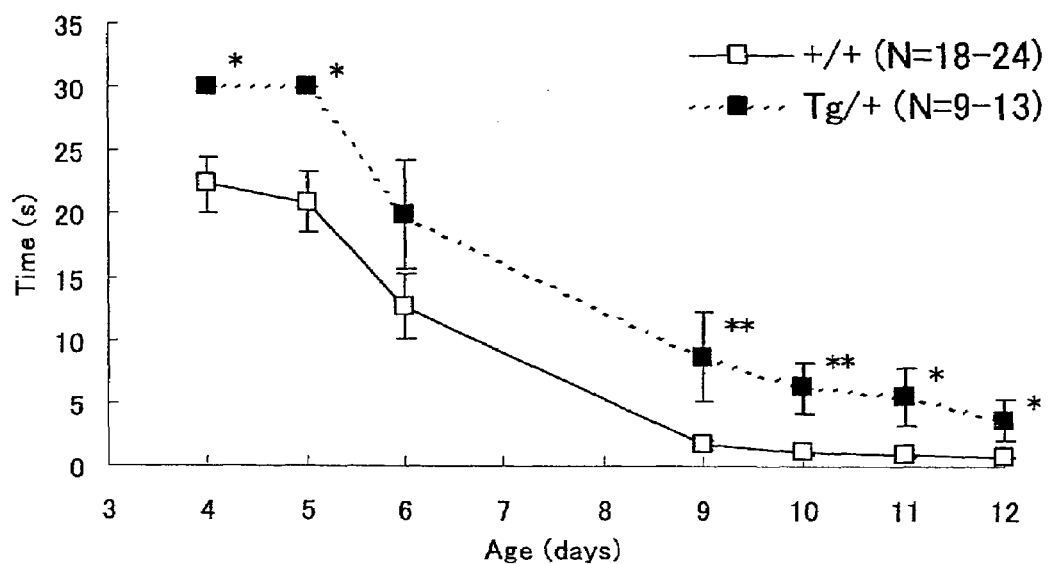
FIG. 4 shows a result of a surface righting reflex test.

In the 1702 line, significantly prolonged reflex latency was observed in the test results of the 12-day-old or younger mice. In wile-type mice, the majority of 10-day-old or older individuals achieved righting reflex within 1 second, whereas individuals, even at 10 days or older of age, among the Tg mice of the 1702 line failed to recover from the lying state for 10 or more seconds (FIG. 4).

Example 11

Spontaneous Locomotor Activity Measurement

The 8-week-old and 1-year-old male mice were used as subjects, and locomotor activities were measured for 1 day using an infrared detection-type motor activity measurement apparatus (AB-System; manufactured by Neuroscience). A light-dark cycle was set to a 12-hour light period (from 7 a.m. to 7 p.m.) and a 12-hour dark period (from 7 p.m. to 7 a.m.). The day before the measurement, the subjects were placed since 7 p.m. in a small, clear polycarbonate cage (L×W× H=23×17×12 cm) with the floor covered with beddings, and were sufficiently acclimatized therein. On the measurement day, the same cage was used to measure locomotor activity once every hour for 24 hours (from 11 a.m. to 11 a.m. of the following day). The locomotor activity was expressed as a cumulative count of 24 hours. Statistical analysis was performed using a significant difference test by Student's t-test.

Figure 5:
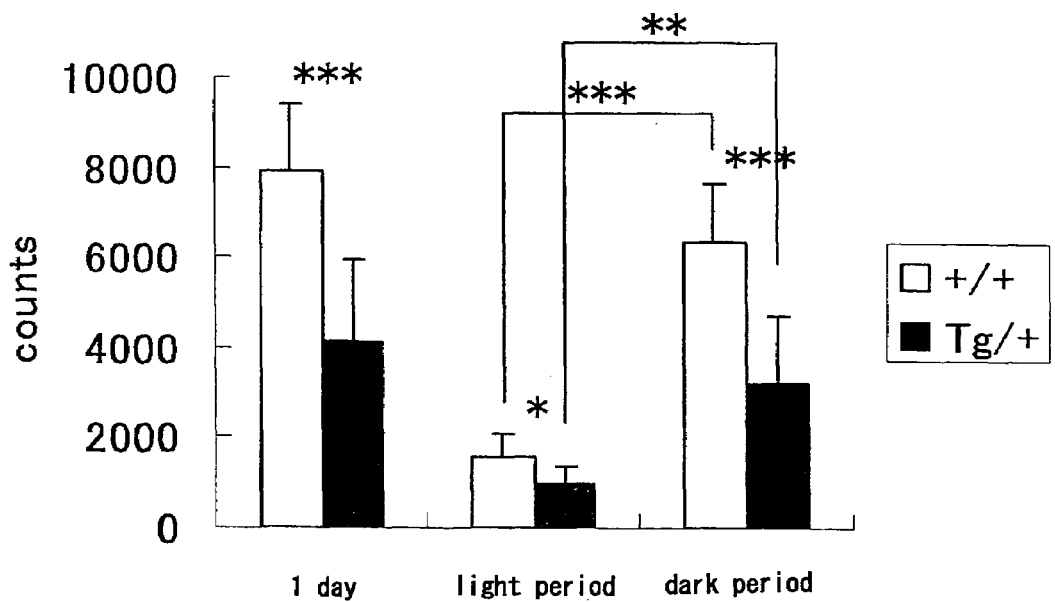
FIG. 5 shows a result of spontaneous locomotor activity measurement.

The whole spontaneous locomotor activity for 1 day was significantly decreased in the 1702 line. This was mainly due to reduction in locomotor activity during the active phase (dark period) (FIG. 5).

Example 12

Intracerebral Monoamine Level Measurement

The midbrain substantial nigra parts and the corpus striata were prepared from the brains of the 8-week-old and 1-year-old mice of the 1702 line, while the whole brains were prepared from the 5-day-old and 10-day-old mice. These tissues were respectively frozen in liquid nitrogen. After the frozen tissues were pulverized with a mill, their weights were measured. The tissues were supplemented with 0.2 M perchloric acid (containing 100 μM disodium ethylenediaminetetraacetate and 10 μM pargyline) in an amount of 0.5 ml/100 mg of the tissue and homogenized using Mini Cordless Grinder (manufactured by Bertec Enterprise). The homogenized samples were stood on ice for 30 minutes and then centrifuged at 0° C. for 20 minutes at 20000×g to collect supernatants. After adjusting pH to approximately 3 with 1 M sodium acetate, the supernatants were passed through a Microcon filter of 0.22 μm in pore size (manufactured by Millipore). The resulting filtrates were used as samples for monoamine measurement.

Monoamine levels were measured by high-performance liquid chromatography (HPLC) under conditions described below. At first, a high concentration of samples (each 1 mg/mL) of seven monoamines (i.e., dopamine: DA, homovanillic acid: HVA, 3,4-dihydroxyphenylacetic acid: DOPAC, L-3-methoxytyramine: 3-MT, norepinephrine: NE, serotonin: 5-HT, and 5-hydroxyindoleacetic acid: 5-HIAA) were prepared, and all of these solutions were mixed and diluted with 0.1 M acetic acid (containing 1 mg/mL disodium ethylenediaminetetraacetate) to prepare a septuple standard sample with the final concentration of 10 ng/μL. The sample was stored under shade at 4° C. until use in order to avoid decomposition.

High Concentration Sample (1 mg/mL)

Distilled water for liquid chromatography (manufactured by Nakarai Tesque) was used in sample preparation.

All the samples were purchased from Sigma.

DA 6.19 mg/5 mL 0.1 N hydrochloric acid (containing 1 mg/mL EDTA-2Na)

HVA 5 mg/5 mL 0.1 N hydrochloric acid (containing 1 mg/mL EDTA-2Na)

DOPAC 5 mg/5 mL 0.1 N hydrochloric acid (containing 1 mg/mL EDTA-2Na)

3-MT 6.09 mg/5 mL 0.1 N hydrochloric acid (containing 1 mg/mL EDTA-2Na)

NE 5 mg/5 mL 0.1 N hydrochloric acid (containing 1 mg/mL EDTA-2Na)

5-HT 6.04 mg/5 mL 0.1M acetic acid (containing 1 mg/mL EDTA-2Na)

5-HIAA 5 mg/5 mL 0.1M acetic acid (containing 1 mg/mL EDTA-2Na)

Next, the standard sample was analyzed by HPLC under conditions described below.

HPLC Analysis Conditions

Column: EICOMPAC SC-5ODS φ 3.0 mm×150 mm (manufactured by Eicom)

Pre-column: guard cartridge (manufactured by Shiseido)

Flow rate: 0.5 mL/min

Working electrode: glassy carbon

Applied voltage: +700 mV

Set temperature: 30° C.

Measurement time: 25 min

Measurement apparatus: NANOSPACE SI-1 Series (manufactured by Shiseido)

Electrochemical detector (SI-1/2005)

Pump (SI-1/2001)

Deaerator (SI-1/2009)

Data analyzer (S-MicroChrom Version 4.1)

Mobile phase composition

| | |
|---|---|
| 0.1 M acetic acid-citric acid solution (pH 3.9) (a mixture solution (pH 3.9) of 0.1 M sodium acetate solution:0.1 M citric acid solution = 10:7) | 82% |
| Methanol (for liquid chromatography) | 18% |
| Sodium 1-octanesulfonate | 190 mg/L |
| Disodium ethylenediaminetetraacetate | 5 mg/L |

At first, the mobile phase for measurement was prepared, and the column was equilibrated with the mobile phase until the measurement value of the electrochemical detector became stable. After the stability of the measurement value was confirmed, the prepared septuple sample was further diluted 200-fold with 0.02 M acetic acid (containing 200 mM disodium ethylenediaminetetraacetate) to the concentration of 500 pg/10 μL which was prepared just before use, and 10 μL thereof was injected into the HPLC system. Peaks from the septuple sample are known to be detected in the order of norepinephrine, 3,4-dihydroxyphenylacetic acid, dopamine, 5-hydroxyindoleacetic acid, homovanillic acid, L-3-methoxytyramine, and serotonin, and the absence of deviation of each peak area and retention time was confirmed. Next, the measurement of the samples extracted from the brain homogenates was performed. The monoamine levels in the samples were measured by automatically injecting 10 μL each of the samples every 25 minutes with an autosampler. Until measurement, the samples were kept at 4° C. in a temperature-controlled bath. The monoamine level was determined by proportionality calculation of the peak area of the sample relative to the peak area of 500 pg/10 μL each of the standard samples and converted to a value per mg of the tissue (5 μL of the sample).

Calculation Method:

Monoamine (pg/mg of tissue)=sample peak area÷standard sample peak area×500 (pg)÷2

Figure 6:
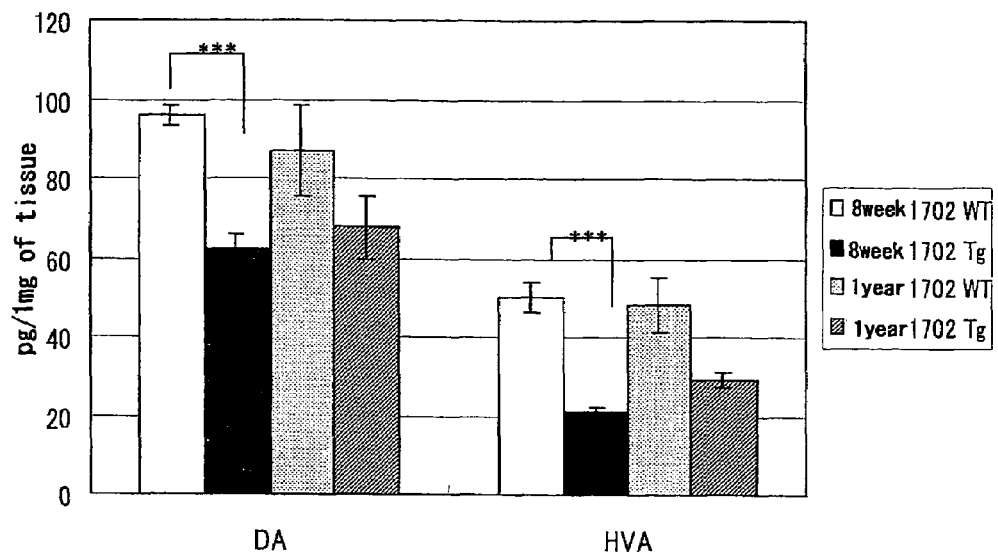
FIG. 6 shows a result of the quantification of monoamine levels in the midbrains of 8-week-old and 1-year-old individuals. DA: dopamine. HVA: homovanillic acid. 5-HT: serotonin.
Figure 6:
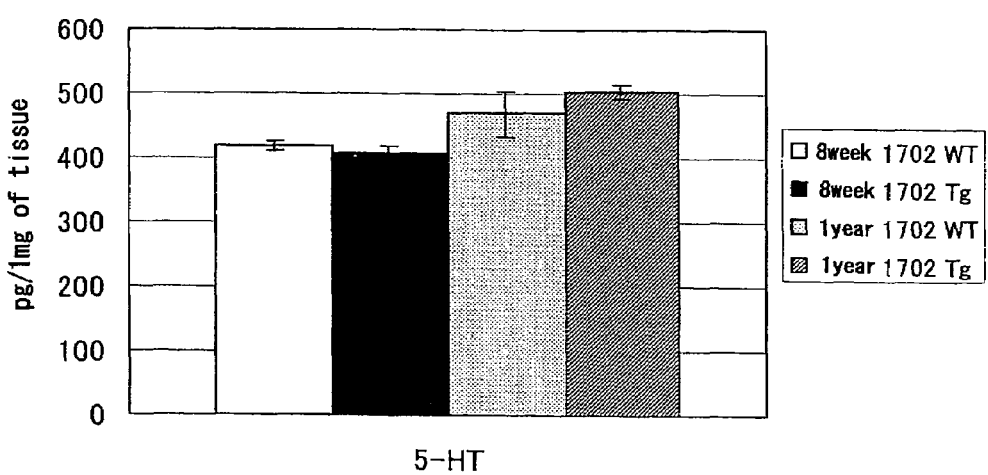
Figure 7:
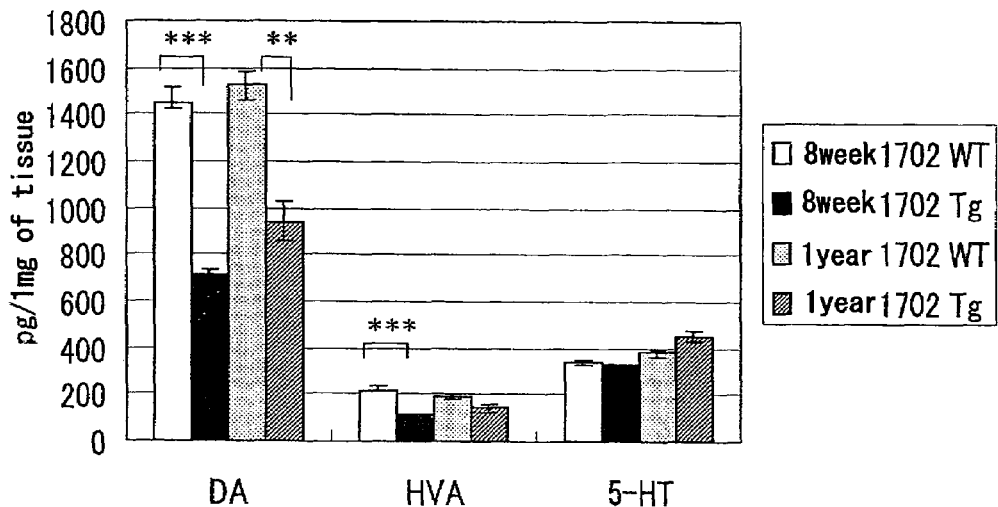
FIG. 7 shows a result of the quantification of monoamine levels in the corpus striata of 8-week-old and 1-year-old individuals. DA: dopamine. HVA: homovanillic acid. 5-HT: serotonin.
Figure 8:
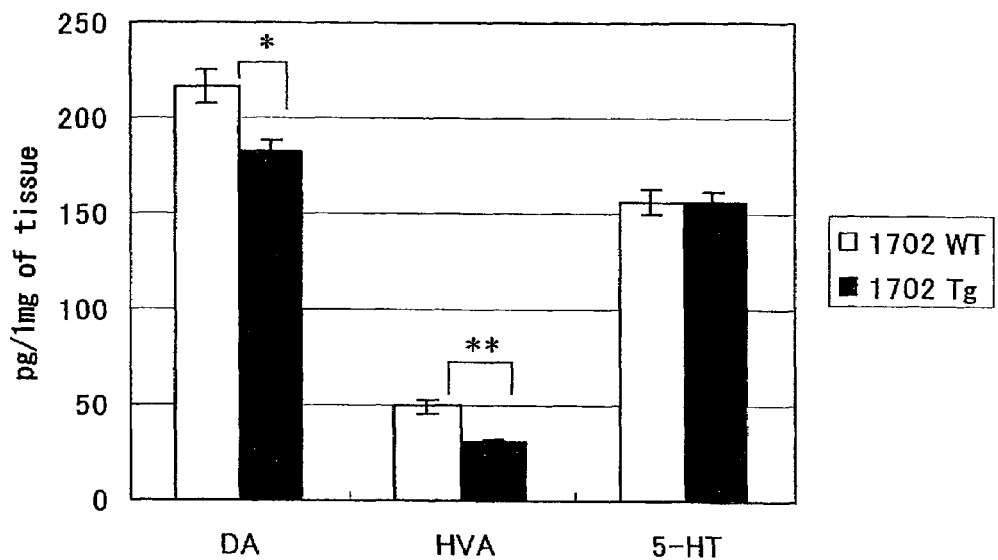
FIG. 8 shows a result of the quantification of monoamine levels in the whole brain of a 5-day-old individual. DA: dopamine. HVA: homovanillic acid. 5-HT: serotonin.
Figure 9:
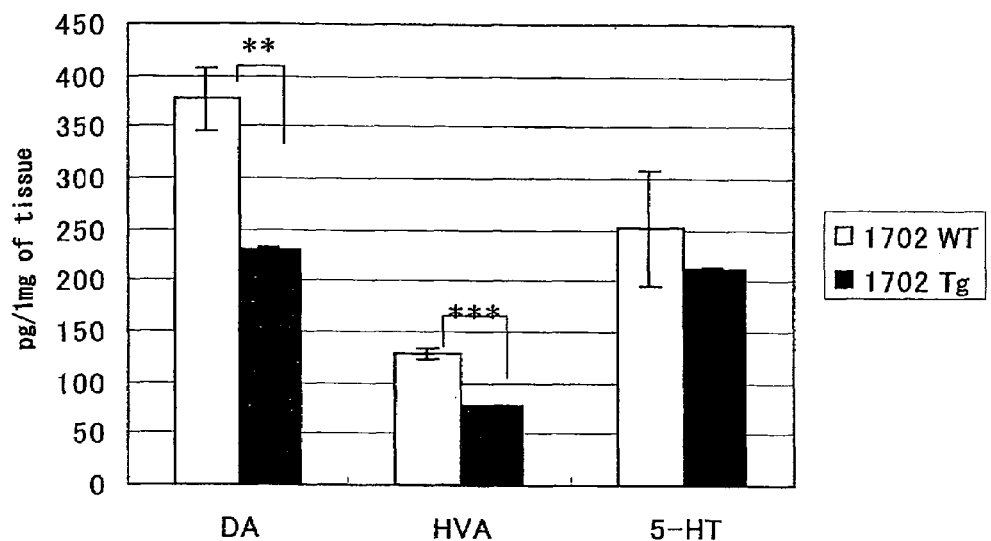
FIG. 9 shows a result of the quantification of monoamine levels in the whole brain of a 10-day-old individual. DA: dopamine. HVA: homovanillic acid. 5-HT: serotonin.

As a result, in the transgenic mice of the 1702 line, their dopamine levels in the midbrain at both 8 weeks of age and 1 year of age were decreased as compared with those of wile-type mice (FIG. 6). Particularly, the dopamine level of the 8-week-old mice was significantly decreased and was approximately 60% of those of wild-type mice. Similarly, the level of homovanillic acid, a metabolite of dopamine, was significantly decreased in the 8-week-old transgenic mice. However, their serotonin levels were not changed. The dopamine levels in the corpus striata were significantly decreased in both of the 8-week-old and 1-year-old mice, and particularly in the 8-week-old mice, the dopamine level was decreased to approximately 50% of those of wild-type mice (FIG. 7). Furthermore, significant decrease in dopamine levels, as in the adult mice, was also observed in the mice at an earlier age (FIGS. 8 and 9). Particularly, the dopamine level of the 10-day-old mice (FIG. 9) was approximately 60% of those of wild-type mice, demonstrating that the dopamine content was remarkably decreased at an age as early as 10 days.

Example 13

Immunohistological Staining

After the dissected brain of the transgenic mouse of the 1702 line was fixed at room temperature for 1 day in Mildform 20NM (manufactured by Wako Pure Chemical Industries), a region between 2 mm at the forebrain side from the bregma and 0 mm from the bregma was cut in the coronal plane using a scalpel and used as a corpus striatum part. Moreover, a region between 2.5 mm posterior to the bregma and 0 mm from the lambda was cut in the coronal plane and used as a midbrain part. Then, these samples were embedded in paraffin according to a routine method and cut into slices to prepare sections of 3 microns in thickness. For antigen activation, the sections were deparaffinized and then treated with a microwave in 10 mM citric acid buffer solution (pH 6.0). The resulting sections were subjected to blocking treatment at 37° C. for 20 minutes using 0.5% blocking reagent/maleic acid buffer solution (100 mM maleic acid and 150 mM sodium chloride, pH 7.5). For immunohistological staining, a rabbit anti-tyrosine hydroxylase antibody (manufactured by Funakoshi, VN-3109-00) diluted 1/100 or a mouse anti-human α-synuclein monoclonal antibody LB509 (manufactured by Cosmo Bio, ZYM180215) diluted 1/2000 was used as a primary antibody, and diluted to the final concentration of 10 μg/ml. Biotinylated anti-rabbit IgG (manufactured by Funakoshi, 41-0510-00) or biotinylated anti-mouse IgG (manufactured by Funakoshi, 41-0520-00) was used as a secondary antibody. The immunohistological staining was performed using an automated immunostaining system (manufactured by Ventana Japan) according to the method recommended by Ventana. At the same time, the cell nuclei were stained with Mayer's hematoxylin (manufactured by Wako Pure Chemical Industries, 131-09665).

Figure 10:
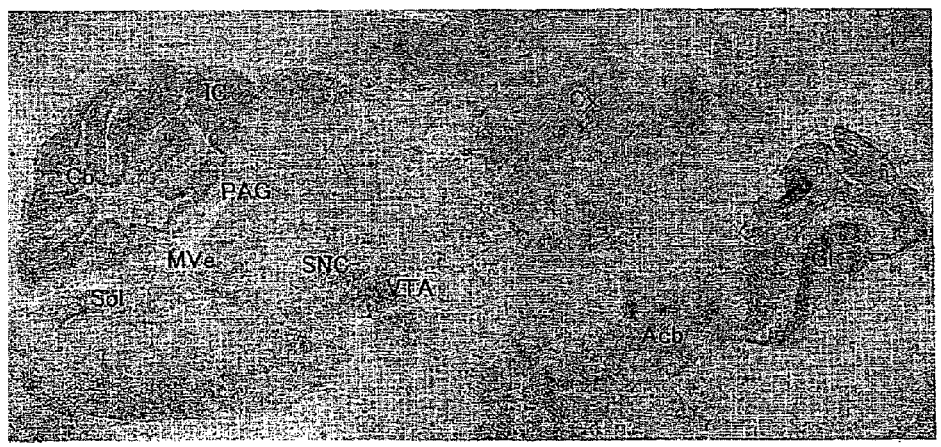
FIG. 10 shows the immunohistological staining of the brain of the 8-week-old individual using LB509.

As a result, a plurality of LB509-positive cells, that is, human α-synuclein-expressing neurons could be found in the midbrain of the transgenic mouse of the 1702 line. Moreover, these LB509-positive neurons were also positive to tyrosine hydroxylase. Therefore, the introduced gene could be confirmed to be expressed in the desired neurons at the desired site (FIG. 10).

Example 14

Quantification of the Number of Tyrosine Hydroxylase-Positive Cells

Figure 11:
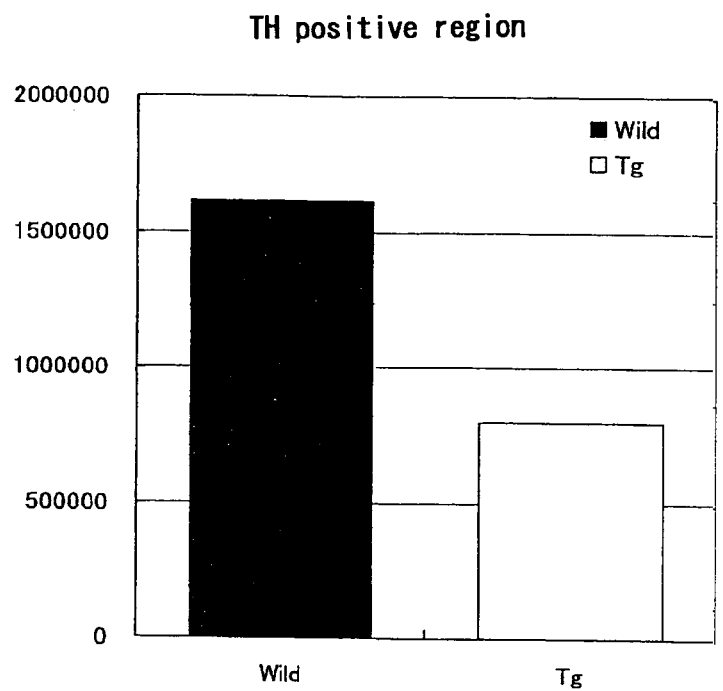
FIG. 11 shows a result of the quantification of tyrosine hydroxylase-positive neurons in the midbrain region of the 8-week-old individual.
Figure 11:
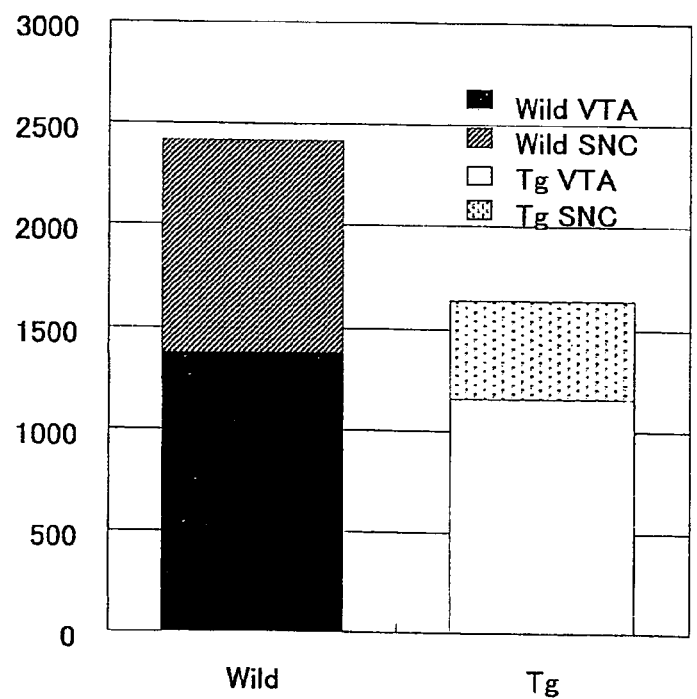

Semi-serial sections of the midbrain of the transgenic mouse of the 1702 line were prepared in a manner described below. At first, 1 section of 3 microns in thickness was taken, and 9 sections of the same thickness were then removed. Theoretically, 1 section of 3 microns in thickness can be obtained per brain tissue of 30 microns in thickness by repeating this procedure. All of the sections thus obtained from the midbrain region were subjected to immunohistological staining using the anti-tyrosine hydroxylase antibody by the same method as described in Example 13. These sections were observed with an optical microscope to thereby select the sections of a region 2.8 mm to 3.8 mm posterior to the bregma. The selected sections were observed so that the left ventral tegmental areas and the substantial nigra pars compacta thereof were placed within a visual field. Image data was captured into a computer using Photograb-2500 (manufactured by FUJIFILM). Subsequently, the image data were printed out, and the number of tyrosine hydroxylase-positive neurons was measured by counting only the neurons having the visible cell nucleus. Alternatively, the quantification of a tyrosine hydroxylase-positive region was performed by analyzing the image data with IPLab software (manufactured by Scanalytics). For this purpose, the total area and the substantial nigra pars compacta area were measured by setting Colar segmentation components to Rs In 98-max so that the tyrosine hydroxylase-positive region in the image was selected. As a result, the tyrosine hydroxylase-positive neurons in the substantial nigra pars compacta of the transgenic mouse of the 1702 line was confirmed to be significantly decreased as compared with those of the same-gender age-matched wild-type mice (FIGS. 11A and 11B).

INDUSTRIAL APPLICABILITY

The transgenic non-human mammal provided by the present invention, which is characterized in that an α-synuclein gene is overexpressed in the brain neurons, wherein the number of dopamine-producing neurons in the substantial nigra is significantly decreased as compared with that of a wild-type animal, is usefull as a model animal of Parkinson's disease in the elucidation of mechanisms underlying Parkinson's disease onset and in the screening of a preventive agent or therapeutic agent for Parkinson's disease. Particularly, the transgenic non-human mammal of the present invention has a significantly decreased level of intracerebral dopamine at 8 weeks of age and as such, has an advantage of having no need to be raised for a long time.

The invention claimed is:

1. A transgenic mouse whose genome comprises a nucleic acid sequence encoding mutant human α-synuclein operably linked to a tyrosine hydroxylase promoter, wherein the mutant human α-synuclein substitutes a Thr residue for a Ala residue at amino acid residue 53 and deletes C terminal amino acid residues, and wherein the number of neurons in the substantia nigra expressing dopamine is decreased as compared to a wild-type mouse.

2. The transgenic mouse according to claim 1, wherein the transgenic mouse has a decrease in dopamine level in corpus striata at an age of at least 8 weeks.

* * * * *

SEQUENCE LISTING

<160> NUMBER OF SEQ ID NOS: 16

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggaattcatt agccatggat gtattc                                          26

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agccacttaa ggaaccagtg catacc                                          26

<210> SEQ ID NO 3

```
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agctctaata cgactcacta taggg                                          25

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cagccactgt tgccacacca tgc                                            23

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
agggttttcc cagtcacgac gttg                                           24

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gcatggtgtg gcaacagtgg ctg                                            23

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tagccttaag ttactcagaa ggcattt                                        27

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtggctgctg ctgagaaaac                                                20

<210> SEQ ID NO 9
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtggggctcc ttcttcattc                                                    20

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aggactgggt ggcttccaac tcccagacac                                          30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
agcttctcat tgctgcgcgc caggttcagg                                          30

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gtggctgctg ctgagaaaac                                                    20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gtggggctcc ttcttcattc                                                    20

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tgtgatggtg ggaatgggtc ag                                                 22

<210> SEQ ID NO 15
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 15
tttgatgtca cgcaccattt cc                                              22

<210> SEQ ID NO 16
<211> LENGTH: 140
<212> TYPE: PRT
<213> ORGANISM: Homo sapiens

<400> SEQUENCE: 16

Met Asp Val Phe Met Lys Gly Leu Ser Lys Ala Lys Glu Gly Val Val
 1               5                  10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
```